May 25, 1965 O. O. DUNHAM Plant Pat. 2,520
CHRYSANTHEMUM PLANT
Filed March 4, 1964
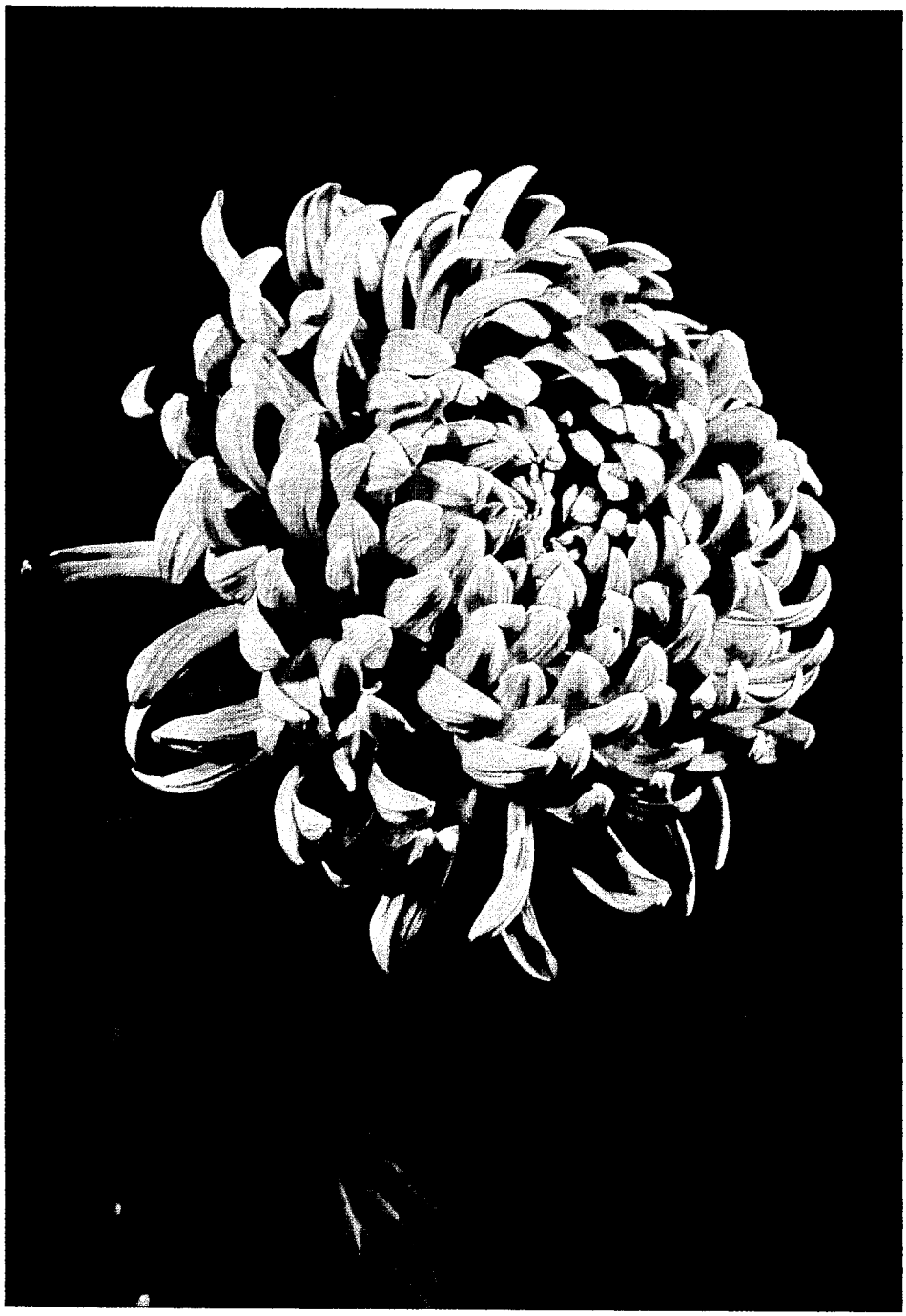
Inventor
O. O. Dunham
by Robb & Robb
attorneys United States Patent Office Plant Pat. 2,520
Patented May 25, 1965

2,520
CHRYSANTHEMUM PLANT

Orville O. Dunham, Niles, Mich., assignor to Stern's Nurseries, Inc., Geneva, N.Y., a corporation of New York Filed Mar. 4, 1964, Ser. No. 349,517
1 Claim. (Cl. Plt.—79)

My present invention comprises a new and distinct variety of chysanthemum plant developed as a result of a number of crossings and specifically crossing of a variety which I designate as #5350, an unpatented variety of my own origination, with another variety, likewise unpatented and which I designate as "Parade," a variety likewise of my own origination.

During the course of an intensive program of breeding, cross breeding and selection, I have developed the instant variety, so as to take advantage of certain of the characteristics of both of the parents, the seed parent, #5350 supplying the earliness to bloom which is found even more desirable under present conditions, with certain of the color characteristics of the pollen parent "Parade."

The instant variety is a large chrysanthemum of attractive form as to the blooms, the blooms being somewhat more reflexed than the parent, "Parade," which has a bronze, very incurved bloom with petals having lighter reverses.

The pollen parent is a somewhat later blooming variety, and thus the earliness to bloom which is provided by the seed parent #5350, is an important factor in the advance provided by the instant variety.

The result of the hybridization to which I have referred previously, has been to produce the present new and distinct variety characterized by the Dark Reddish-Orange inside of the petals with Orange-Yellow reverses providing a Reddish-Bronze general tonality, the large incurving blooms, somewhat reflexed, enjoying an earliness to bloom which makes the same more attractive, and the blooms appearing on strong, upright stems and the plant itself having excellent weather resistant characteristics.

More specifically, the blooms of my new variety are of an overall bronze tonality, in which the inner faces of the petals are of the Dark Reddish-Orange heretofore mentioned, the reverses being Moderate Orange-Yellow and thereby affording the bronzish tone which makes the plant attractive (Nickerson Color Fan published by the Munsell Color Company).

As the plant has been grown in the vicinity of Niles, Michigan, in uniform culture, the variety grows to a height of 20 inches on upright plants, with straight, stiff stems, a profusion of blooms being common.

My new variety derives a number of characteristics from both parents, but the better characteristics are retained, the aforementioned early blooming and general color, the latter being somewhat more reddish than the parent "Parade." My new variety differs from both of its parents and from other known varieties in the aspects heretofore suggested.

Under the conditions of culture previously mentioned, which took place in the region of Niles, Michigan, plants of my new variety grow vigorously with profuse foliage from mid-September until a killing frost.

My new variety, when grown in the region of Niles, Michigan, blooms continuously during this period and has large incurved blooms from 6 to 7 inches in diameter.

My new variety has been asexually reproduced by cuttings in the vicinity of Niles, Michigan, observations made herein as a basis for the subsequent description having been made during mid-October.

My new variety has been found to retain its distinctive characteristics through successive asexual reproduction.

In the accompanying drawing there is disclosed a bloom of my new variety, in a color illustration which is as near characteristic as is possible and in color which is reasonably accurate as provided in color illustrations of this nature.

The following is a detailed description of my new variety of chrysanthemum plant, the color references being to the Nickerson Color Fan published by the Munsell Color Company:

*Description*

Parentage: Seedling.
- *Seed parent.*—#5350 (unpatented).
- *Pollen parent.*—"Parade" (unpatented).

Classification: Botanic—*Chrysanthemum indicum.*

*Flower*

Blooming Habit: Blooms profusely and continuously from mid-September until a killing frost.

Bud:
- *Size.*—Large.
- *Form.*—Short with flat top. Not affected substantially by hot or wet weather.
- *Sepals.*—Of no consequence.
- *Calyx.*—Shape—funnel. Size—large and broad. Aspect—hairy.
- *Peduncle.* — Length — medium. Aspect — rough. Strength—stiff and erect. Bud opens well and is not affected by adverse conditions.

Bloom:
- *Size.*—Very large. Average size when fully expanded—6 to 7 inches.
- *Borne.*—In clusters and pyramidal.
- *Stems.*—Long and strong.
- *Form.*—When first open—cupped. Permanence—retains its form to the end.
- *Petalage.*—Very double. Innumerable petals under normal conditions.

Color:
- *Center of flower.*—10R 5/11 Strong Reddish-Orange.
- *Outer petals.*—10R 6/12 Strong Reddish-Orange.
- *Base of petals.*—10R 4/9 Dark Reddish-Orange.
- *Inside of petals.*—10R 4/9 Dark Reddish-Orange.
- *Reverse of petals.*—10YR 8/10 Moderate Orange-Yellow.
- *General tonality combination.*—Bronzish mixture of Dark Reddish-Orange and Moderate Orange-Yellow.
- *Discoloration.*—General tonality at end of: First week—same as when bloom opens. Second week—retains same color. Third week—retains same color.

Petals:
- *Texture.*—Thick and soft. Not affected by hot or wet weather.
- *Appearance.*—Inside—velvety. Outside—satiny.
- *Form.*—Oval.
- *Arrangement.*—Irregular.
- *Persistence.*—Hang on and dry.
- *Lastingness:* On the plant—very long. As cut flower—very long.

Genital organs:
- *Stamens, anthers.*—Small, few.
- *Arrangement.*—Regular around styles.
- *Stamens, filaments.*—Medium.
- *Styles.*—Columnar.
- *Ovaries.*—All enclosed in calyx.

Plant:

*Form.*—Bush.

*Growth.*—Vigorous, upright and branching.

Foliage:

*Size.*—Very large.

*Quantity.*—Abundant.

*Texture.*—Upper side—glossy. Under side—velvety.

*Ribs and veins.*—Ordinary.

*Edge.*—Serrated.

*Serration.*—Single.

I claim:

A new and distinct variety of chysanthemum plant substantially as herein disclosed characterized as to novelty by the Dark Reddish-Orange inside of petals with Orange-Yellow reverses, providing a Reddish-Bronze general tonality, large, incurving blooms, somewhat reflexed, earliness to bloom, and strong, upright habit of growth with good weather resistant characteristics.

No references cited.

ABHAHAM G. STONE, *Primary Examiner.*